United States Patent [19]

Imran

[11] Patent Number: 6,022,374
[45] Date of Patent: Feb. 8, 2000

[54] EXPANDABLE STENT HAVING RADIOPAQUE MARKER AND METHOD

[75] Inventor: Mir A. Imran, Los Altos Hills, Calif.

[73] Assignee: CardioVasc, Inc., Menlo Park, Calif.

[21] Appl. No.: 08/991,378

[22] Filed: Dec. 16, 1997

[51] Int. Cl.[7] .................................................... A61F 2/06
[52] U.S. Cl. ................................................................. 623/1
[58] Field of Search ..................................... 623/1, 11, 12

[56] References Cited

U.S. PATENT DOCUMENTS

| | | | |
|---|---|---|---|
| 5,632,771 | 5/1997 | Boatman | 623/1 |
| 5,725,572 | 3/1998 | Lam | 623/1 |
| 5,824,042 | 10/1998 | Lombardi | 623/1 |

*Primary Examiner*—Michael J. Milano
*Attorney, Agent, or Firm*—Flerh Hohbach Test Albritton & Herbert

[57] ABSTRACT

An expandable stent having a radiopaque marker therein comprising a cylindrical member having a wall defining a central bore extending along a longitudinal axis and having inner and outer surfaces and a length. The wall has a pattern formed therein with openings extending therethrough into the bore. At least one radiopaque marker is carried by the wall and is disposed in an opening in the wall. The radiopaque marker is comprised of a framework formed in the wall and is disposed in an opening in the wall and lies within the confines of the wall. The framework is isolated from the pattern so that it does not interfere with the expansion of the expandable stent. The framework has an eyelet therein. An insert formed of a radiopaque material is disposed in the eyelet and retained in the framework and lies within the confines of and is flush with the inner and outer surfaces of the wall.

8 Claims, 3 Drawing Sheets

EXPANDABLE STENT HAVING RADIOPAQUE MARKER AND METHOD

This invention relates to an expandable stent having a radiopaque marker and a method for fabricating the radiopaque marker.

Stents herebefore have been provided typically are formed of stainless steel and other metals, which in and of themselves are not readily visible in fluoroscopic imaging systems. It has been found that it is important to be able to visualize the stents during the time that they are being deployed and also to be able to visualize the stents after they have been deployed, at periodic time intervals. Attempts have been made to make such stents more radiopaque by brazing gold or platinum onto the stents. However, even though the desired radiopacity may be achieved, such approaches have not been found to be particularly satisfactory in that the brazing process may cause local annealing of the stent, and may change its mechanical properties. There is therefore a need for a new and improved radiopaque marker for use on stents.

In general, it is an object of the present invention to provide an expandable stent having a radiopaque marker and a method for fabricating the same.

Another object of the invention is to provide an expandable stent with a radiopaque marker in which the radiopaque marker does not experience stresses or strains during expansion of the stent.

Another object of the invention is to provide an expandable stent having a radiopaque marker in which the radiopaque marker is isolated from the stent pattern so that it does not interfere with the expansion of the stent.

Another object of the invention is to provide an expandable stent with a radiopaque marker of the above character in which the radiopaque marker does not protrude from the exterior surface or the interior surface of the stent.

Another object of the invention is to provide a radiopaque marker which can be readily and economically fabricated.

Additional objects and features of the invention will appear from the following description in which the preferred embodiment is set forth in conjunction with the accompanying drawings.

In general, the stent having a radiopaque marker therein is comprised of a cylindrical member having a wall defining a central bore extending along a longitudinal axis and having an outside diameter and an inside diameter and a length. The wall has a pattern formed therein with openings therein. At least one radiopaque marker is carried by the wall and is disposed in an opening. The radiopaque marker is comprised of a framework formed in the wall and lying within the inner and outer confines of the wall and is carried by the wall and is disposed in an opening in the pattern so that it is isolated from the pattern so that it does not interfere with the expansion of the stent. The framework has an eyelet therein and an insert formed of a radiopaque material is secured in the stent and lies within the confines of the inner wall and the outer wall.

In general, the method for forming a radiopaque marker for use with a cylindrical stent having a wall defining a bore extending therethrough and having an outside diameter and inside diameter and a longitudinal axis with the wall of the stent having a pattern with openings therein. The method comprises forming an eyelet in the wall of the stent so that it is disposed in at least one of the openings in the wall. An insert is provided which has a volume which corresponds to the volume of the eyelet and is mounted in the eyelet so that it is retained in the eyelet and lies within the confines of the inner and outer diameter of the wall.

Figure 1:
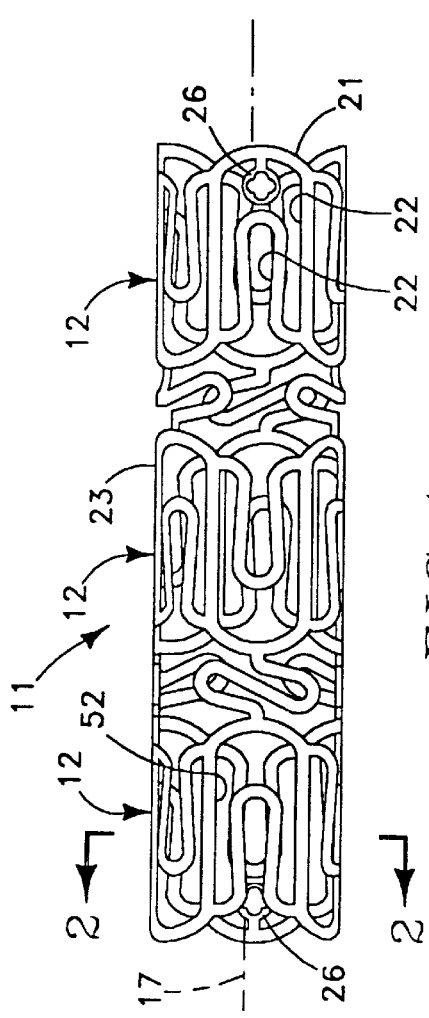
FIG. 1 is a side elevational view of a stent having a radiopaque marker incorporating the present invention.
Figure 2:
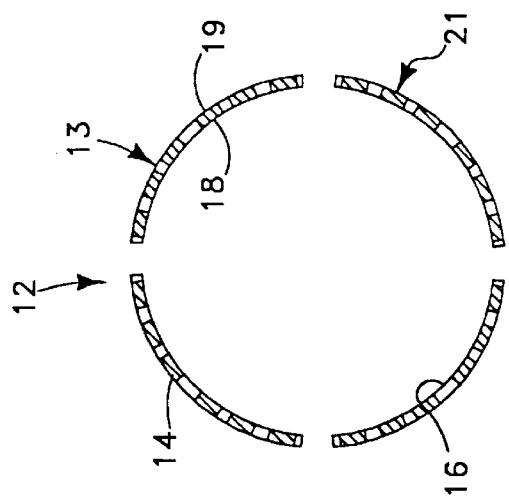
FIG. 2 is a cross-sectional view taken along the line 2—2 of FIG. 1.

More in particular, a stent 11 utilized in conjunction with the radiopaque marker of the present invention is shown in FIG. 1 and consists of at least one segment 12 and generally a plurality of segments 12. Each segment 12 is comprised of a cylindrical member 13 which has a wall 14 formed of a suitable metal such as stainless steel which defines a bore 16 extending along a longitudinal axis 17. The wall 14 has a thickness so that there is provided an inside surface 18 and an outside surface 19. A pattern 21 is provided in the wall and has a plurality of openings 22 extending through the wall.

The stent 11 hereinbefore described is merely one stent on which the radiopaque marker 26 of the present invention can be used. The characteristics of the particular stent 11 shown in FIG. 1 are described in detail in co-pending application Ser. No. 08/99/,378 filed Dec. 16, 1997 and the more detailed features thereof are incorporated herein by reference.

At least one radiopaque marker 26 is provided in the stent 11. However, it is generally desirable to provide more than one radiopaque marker 26 to ascertain the position of the stent and as well, and in many cases, to ascertain the expansion of the stent, the longitudinal positioning of the stent to ascertain whether or not the stent has moved after elapse of periods of time as for example, after a period of six months or twelve months.

Figure 3A:
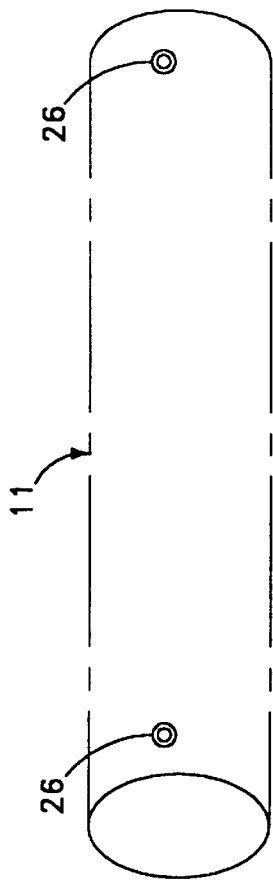
FIGS. 3A, 3B and 3C illustrate various placements of radiopaque markers on stents and incorporating the present invention in stents.
Figure 3B:
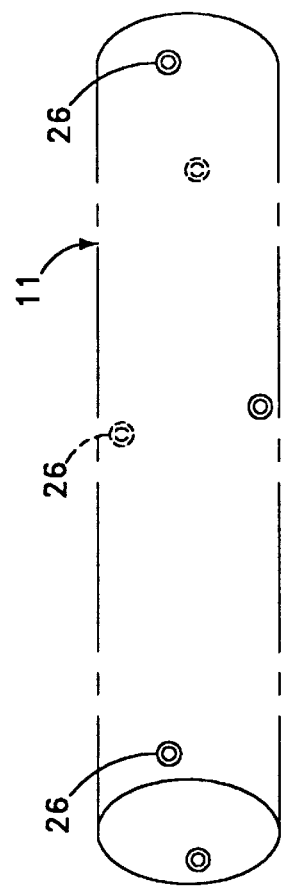
Figure 3C:
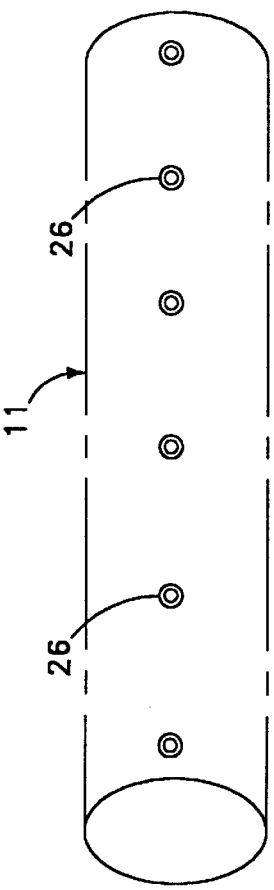

Different patterns for use of the radiopaque markers are shown in FIGS. 3A, 3B and 3C. In FIG. 3A, a radiopaque marker 26 is provided in opposite ends of the stent 11. In FIG. 3B, radiopaque markers 26 are provided at opposite ends of the stent 11 and also at an intermediate point of the stent with radiopaque markers 26 also being disposed in each location at diametrically opposite points so that the amount of radial expansion of the stents can be ascertained by observing the locations of the radiopaque markers. In FIG. 3C, a plurality of radiopaque markers 26 are provided which are spaced apart equi-distant along the length of the stent to make possible observation of the elongation or shortening of the stent during expansion.

Figure 1A:
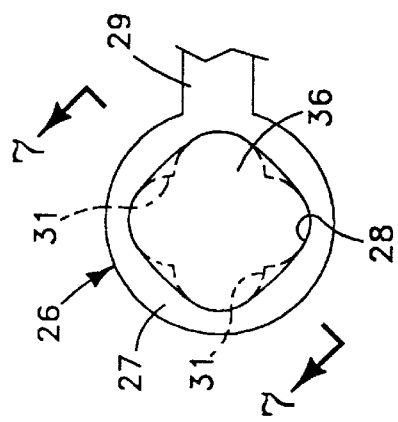
FIG. 1A is an enlarged view taken from FIG. 1 of a radiopaque marker shown in FIG. 1.
Figure 4:
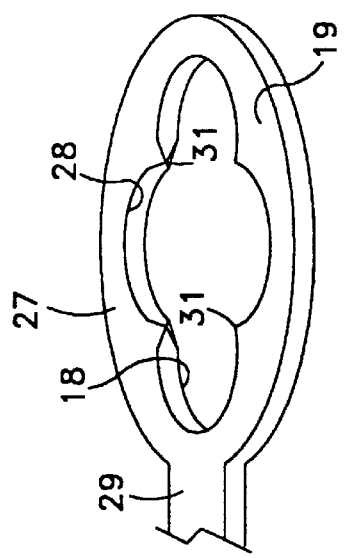
FIG. 4 is an enlarged isometric view of the framework provided in the radiopaque marker of the present invention and showing an eyelet provided by the framework.

Each of the radiopaque markers 26 consists of a framework 27 which is provided with an eyelet 28 therein (see FIGS. 1A and 4). The framework 27 with the eyelet 28 therein typically is formed in the wall 14 during the same time that the pattern 21 is formed and is connected by a link 29 to the pattern. Such a pattern can be formed by laser cutting or etching. It is important that the framework 27 have the same wall thickness as the wall 14 itself and therefore it is preferable that it be formed of the wall 14 and in the wall 14 so that the framework 27 is disposed in one of the openings 22 in the pattern 21 so that it is not subjected to stresses and strains during expansion of the stent and also so that it does not interfere with the expansion of the stent.

The framework 27 is provided with a plurality of circumferentially spaced-apart substantially conical protrusions or projections 31 which are cone shaped as shown in FIGS. 3 and 4 and lie within the confines of the inner and outer surfaces 18 and 19 of the wall 14. A plurality of such projections 31 are provided in accordance with the present invention and it is desirable to have at least three of such inwardly and radially extending projections and preferably four as shown, but as many as eight.

The radiopaque marker 26 also includes an insert 36 which is formed of a suitable radiopaque material such as gold or platinum or alloys thereof. To provide such an insert 36, the volume of the eyelet 28 between the inner and outer surfaces 18 and 19 of the wall, taking into account the volume occupied by the protrusions or projections 31 is precisely calculated. By way of example, as shown in FIG. 3 such projections can be provided with the eyelet having a diameter of 0.015 inches and having an inner diameter of 0.010 inches extending between two opposite protrusions or projections 31 with each of the projections extending inwardly by a distance of 0.0025 inches with the wall being of a suitable thickness as for example 0.003 inches.

Figure 6:
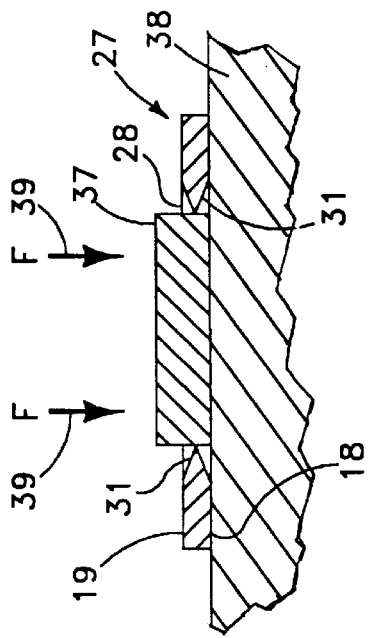
FIG. 6 is a cross-sectional illustration showing the manner in which an insert is placed in an eyelet by use of a mandrel in a stent.
Figure 7:
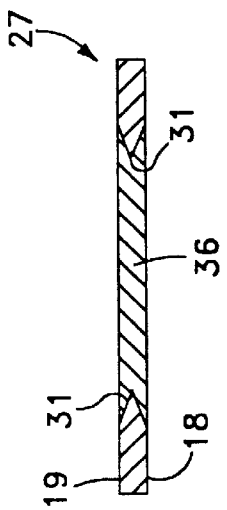
FIG. 7 is a cross-sectional view of the radiopaque marker after the insert has been forged into the eyelet in accordance with the method of the present invention.
Figure 5:
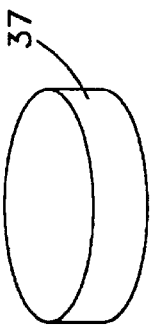
FIG. 5 is an isometric view of an insert as provided to fit within the eyelet shown in FIG. 3.

As soon as the volume of the eyelet 28 has been ascertained, and knowing the diameter, a calculation is made of the desired thickness for a cylindrical plug 37. A sheet of the desired radiopaque material is selected as for example of platinum or gold, having a suitable thickness as for example 0.008 mls. Since the plug 37 must be of a suitable diameter to as for example 0.010 inches when it is disposed between the projections or spikes 31, the additional volume required is obtained by providing the additional volume in the thickness of the plug which can be obtained by providing a sheet (not shown) of radiopaque material and then rolling it down to the desired thickness to achieve the desired volume for the plug 47 when it is punched up from the sheet. A cylindrical plug 37 (see FIG. 5) of the desired diameter is punched therefrom. The plug 37 is then taken and placed in the eyelet 28 of the framework 27 carried by the stent with a cylindrical tight fitting mandrel 38 being disposed within the stent as shown in FIG. 6. A suitable force is then applied as for example by an arbor press as indicated by the "F" arrows 39 to press and forge the plug 37 into the eyelet 28 so that it completely fills the volume of the eyelet 28 and so that it overlies and underlies the protrusions 31 within the confines of the inner and outer surfaces 18 and 19, so that it does not protrude from the wall but is substantially flush with both surfaces thereof. Thus the material of the plug 37 is forced to flow over the eyelets 28 and thereby be cold forged into the eyelet 28.

It can be seen that this formation of a radiopaque marker or markers in the stent 11 can be accomplished without interfering with the mechanical properties of the stent itself. The method then makes it possible to securely mount the insert within the eyelet to ensure that it will not accidentally pop out. Also, it can be seen that the method provided has made it possible to capture the radiopaque material so that a robust mechanically reliable construction is provided which provides the desired radiopacity needed to observe the stent as hereinbefore described. Thus, it can be seen that it is possible to provide a plurality of radiopaque markers in a stent. Typically, these can be incorporated into the stent one by one by longitudinal movement or rotation of the stent in the arbor during insertion of the inserts into the eyelets of the radiopaque markers. Thus it can be seen that a plurality of radiopaque markers can be provided on a stent in a feasible and economic manner.

What is claimed:

1. An expandable stent having a radiopaque marker therein comprising a cylindrical member having a wall defining a central bore extending along a longitudinal axis and having inner and outer surfaces and a length, the wall having a pattern formed therein with openings extending therethrough into the bore, at least one radiopaque marker carried by the wall and disposed in an opening in the wall, the radiopaque marker being comprised of a framework formed in the wall and disposed in an opening in the wall and lying within the confines of the wall, said framework being isolated from the pattern so that it does not interfere with the expansion of the expandable stent, the framework having an eyelet therein and an insert formed of a radiopaque material disposed in the eyelet and retained in the framework and lying within the confines of and being flush with the inner and outer surfaces of the wall.

2. A stent as in claim 1, wherein said framework is provided with at least three protrusions.

3. An expandable stent having a radiopaque marker therein comprising a cylindrical member having a wall defining a central bore extending along a longitudinal axis and having inner and outer surfaces and a length, the wall having a pattern formed therein with openings extending therethrough into the bore, at least one radiopaque marker carried by the wall and disposed in an opening in the wall, the radiopaque marker being comprised of a framework formed in the wall and disposed in an opening in the wall and lying within the confines of the wall, said framework being isolated from the pattern so that it does not interfere with the expansion of the expandable stent, the framework having an eyelet therein and an insert formed of a radiopaque material disposed in the eyelet and retained in the framework and lying within the confines of the inner and outer surfaces of the wall, said framework being provided with circumferentially spaced apart protrusions extending into the eyelet and projecting into the insert to aid in retaining the insert within the eyelet.

4. A stent as in claim 3 wherein said protrusions are conical in shape and lie within the confines of the inner and outer surfaces of the wall.

5. A method for forming a radiopaque marker in a cylindrically stent having a wall defining a bore extending along a longitudinal axis, the wall of the stent having inner and outer surfaces and having a pattern therein with openings extending therethrough comprising forming at least one eyelet in the wall of the stent in at least one of the openings in the wall and having a volume, providing an insert of a radiopaque material that has a volume corresponding to the volume of the eyelet and pressing the insert into the eyelet so that it is retained in the eyelet and so that the insert lies within the confines of and is flush with the inner and outer surfaces of the wall.

6. A method as in claim 5, together with the step of providing a close-fitting mandrel within the bore of the stent and thereafter pressing the insert into the eyelet against the mandrel while the mandrel is within the bore of the stent.

7. A method as in claim 6 together with the step of providing additional radiopaque markers on the stent utilizing the same mandrel.

8. A method for forming a radiopaque marker in a cylindrically stent having a wall defining a bore extending along a longitudinal axis, the wall of the stent having inner and outer surfaces and having a pattern therein with openings extending therethrough comprising forming at least one eyelet in the wall of the stent in at least one of the openings in the wall and having a volume, providing an insert of a radiopaque material that has a volume corresponding to the volume of the eyelet and pressing the insert into the eyelet so that it is retained in the eyelet and so that the insert lies within the confines of the inner and outer surfaces of the wall and forming a plurality of circumferentially spaced apart protrusions in the eyelet so that the insert must be formed around the projections when the insert is pressed into the eyelet.

* * * * *